(12) United States Patent  (10) Patent No.: US 8,118,488 B2
Gregerson  (45) Date of Patent: Feb. 21, 2012

(54) MOBILE MEDICAL IMAGING SYSTEM AND METHODS

(75) Inventor: Eugene A. Gregerson, Bolton, MA (US)

(73) Assignee: Mobius Imaging, LLC, Ayer, MA (US)

( * ) Notice: Subject to any disclaimer, the term of this patent is extended or adjusted under 35 U.S.C. 154(b) by 28 days.

(21) Appl. No.: 12/576,681

(22) Filed: Oct. 9, 2009

(65) Prior Publication Data

US 2010/0172468 A1 Jul. 8, 2010

Related U.S. Application Data

(60) Provisional application No. 61/142,494, filed on Jan. 5, 2009.

(51) Int. Cl.
 *H05G 1/02* (2006.01)
(52) U.S. Cl. ........................ 378/198; 378/196
(58) Field of Classification Search .............. 378/20, 378/102, 193, 195, 196, 197, 198
See application file for complete search history.

(56) References Cited

U.S. PATENT DOCUMENTS

| | | | |
|---|---|---|---|
| 4,928,283 A | 5/1990 | Gordon | |
| 4,935,949 A | 6/1990 | Fujita et al. | |
| 4,977,588 A | 12/1990 | Van der Ende | |
| 5,448,607 A | 9/1995 | McKenna | |
| 5,448,608 A | 9/1995 | Swain | |
| 5,638,419 A | 6/1997 | Ingwersen | |
| 5,784,428 A | 7/1998 | Schmidt | |
| RE36,099 E * | 2/1999 | Gordon | 378/20 |
| 6,195,578 B1 | 2/2001 | Distler et al. | |
| 6,212,251 B1 | 4/2001 | Tomura et al. | |
| 6,322,251 B1 | 11/2001 | Ballhaus et al. | |
| 6,366,796 B1 | 4/2002 | Yanof et al. | |
| 6,456,684 B1 | 9/2002 | Mun et al. | |
| 6,609,826 B1 | 8/2003 | Fujii et al. | |
| 6,618,613 B1 | 9/2003 | Shukla et al. | |
| 6,940,941 B2 | 9/2005 | Gregerson et al. | |
| 6,959,068 B1 | 10/2005 | Sommer | |
| 7,001,045 B2 | 2/2006 | Gregerson et al. | |
| 7,338,207 B2 | 3/2008 | Gregerson et al. | |
| 7,388,941 B2 | 6/2008 | Sukovic et al. | |
| 7,438,471 B2 | 10/2008 | Tybinkowski et al. | |
| 2005/0135560 A1 | 6/2005 | Dafni et al. | |
| 2007/0092068 A1 | 4/2007 | Albert | |
| 2007/0183588 A1 | 8/2007 | Bailey et al. | |

OTHER PUBLICATIONS

Jupiter system brochure (Nov. 2008) from TRUMPF Medezin Systeme GmbH & Co. KG of Puchheim, Germany.

* cited by examiner

*Primary Examiner* — Hoon Song
(74) *Attorney, Agent, or Firm* — The Marbury Law Group, PLLC

(57) ABSTRACT

A mobile medical imaging device that allows for multiple support structures, such as a tabletop or a seat, to be attached, and in which the imaging gantry is indexed to the patient by translating up and down the patient axis. In one embodiment, the imaging gantry can translate, rotate and/or tilt with respect to a support base, enabling imaging in multiple orientations, and can also rotate in-line with the support base to facilitate easy transport and/or storage of the device. The imaging device can be used in, for example, x-ray computed tomography (CT) and/or magnetic resonance imaging (MRI) applications.

105 Claims, 16 Drawing Sheets

MOBILE MEDICAL IMAGING SYSTEM AND METHODS

CROSS-REFERENCE TO RELATED APPLICATION

This application claims the benefit of U.S. Provisional Application No. 61/142,494, filed Jan. 5, 2009.

STATEMENT REGARDING FEDERALLY SPONSORED RESEARCH OR DEVELOPMENT

N/A

BACKGROUND OF THE INVENTION

The present invention is in the technical field of medical imaging, including, for example, mobile computed tomography and magnetic resonance imaging devices.

Conventional computed tomography (CT) and magnetic resonance (MR) imaging devices, are typically either immovable or exceedingly difficult to transport and consist of multiple components including the imaging gantry and a separate imaging table. It is difficult to move these devices throughout a hospital because they have not been designed to fit though standard hallways and the imaging table top is unusable or unfit for procedures other than standard diagnostic imaging or do not allow imaging with the patient in a sitting position. In addition, a separate single procedure specific table top is generally indexed to translate into and out of the imaging device throughout a procedure thus limiting its practical applications beyond diagnostic imaging. Moving such devices typically requires several strong persons, or a sturdy wheeled vehicle such as a reinforced wagon or hand cart. The difficulties of moving such a device throughout a hospital or office are multiplied when the device needs to be moved from one floor to another. Further, it is not an uncommon experience to realize that the device cannot pass through the doorway without its widening. Further, the devices cannot readily be moved from spot to spot once inside a room.

BRIEF SUMMARY OF THE INVENTION

In accordance with the present invention, an easily transportable mobile medical imaging device is disclosed. The mobile medical imaging device allows for multiple procedural support structures, such as a surgical table or a seat, to be attached. An imaging gantry is provided that is indexed to the patient by translating up and down the patient axis. In a preferred embodiment, the imaging gantry can translate, rotate and/or tilt with respect to a support base, enabling imaging in multiple orientations, and can also rotate in-line with the support base to facilitate easy transport and/or storage of the device. The imaging device can be used in, for example, x-ray computed tomography and/or magnetic resonance imaging (MRI) (magnetic resonance) applications.

According to one embodiment, a medical imaging system comprises a base; a pedestal mounted to the base; a gimbal support mounted to the base; and a gantry ring that is attached to the gimbal support and is suspended above the top surface of the base. The gantry ring includes an image collection apparatus, such as an x-ray source and an x-ray detector array, for obtaining image data from an object located within the bore of the gantry ring. The gantry ring can translate in a first direction relative to the base and rotate at least about 90 degrees with respect to an axis extending generally normal to the top surface of the base. In certain embodiments, the gantry ring can also tilt with respect to the gimbal support.

The gimbal support can be a generally U-shaped support having arms extending upwards from the base and connecting to opposite sides of the gantry ring. The gimbal support can translate and rotate with respect to the base in order to translate and rotate the gantry ring on the base. The base is preferably a mobile base having one or more wheels attached to the base.

The imaging system can further comprise a tabletop support mounted to and disposed above the pedestal, the tabletop support extending at least partially into the bore of the gantry ring. The tabletop support can support an object, typically an individual or an animal to be imaged. The tabletop support can be detachable from the pedestal, and the pedestal can be adapted to support any one of a plurality of interchangeable tabletop supports, including, for example, surgical or trauma tables, modular tabletops, and chairs for imaging of a seated patient. The system can include means for adjusting the height of the tabletop support relative to the base, as well as for translating the tabletop support in one or more directions relative to the pedestal.

The gantry ring can have a relatively large imaging bore having a diameter greater than about 38 inches and generally between about 40 and 50 inches. The overall dimensions of the gantry ring are generally relatively small in order to improve the portability of the system. For example, the outer diameter of the gantry is generally less than about 70 inches and the width of the gantry ring is typically about 17 inches or less.

In certain embodiments, the gantry ring rotates with respect to the base between an imaging position, in which the bore of the gantry ring is faced generally in the direction of the pedestal, and a transport position, in which the bore is faced generally perpendicular to the pedestal and in-line with the base. By rotating the gantry ring into the transport position, the overall width of the system is reduced, which allows for easier transport of the system through doors and hallways.

The present invention further includes methods of imaging an object using an imaging system as described above.

BRIEF DESCRIPTION OF THE SEVERAL VIEWS OF THE DRAWINGS

Other features and advantages of the present invention will be apparent from the following detailed description of the invention, taken in conjunction with the accompanying drawings of which.

DETAILED DESCRIPTION OF THE INVENTION

This application claims the benefit of U.S. Provisional Application No. 61/142,494, filed Jan. 5, 2009, the entire teachings of which are incorporated herein by reference.

Figure 1:
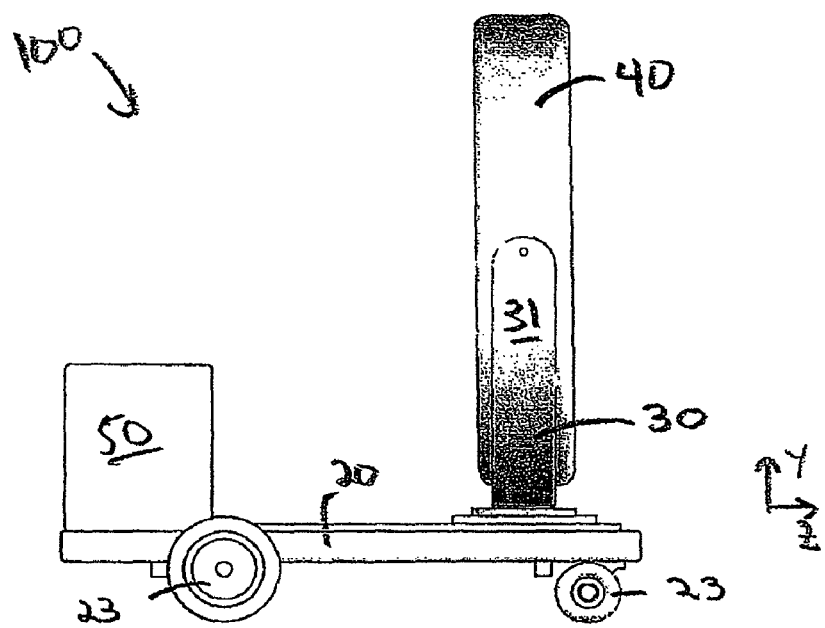
FIG. 1 is a side view of a mobile imaging system of the invention.
Figure 2:
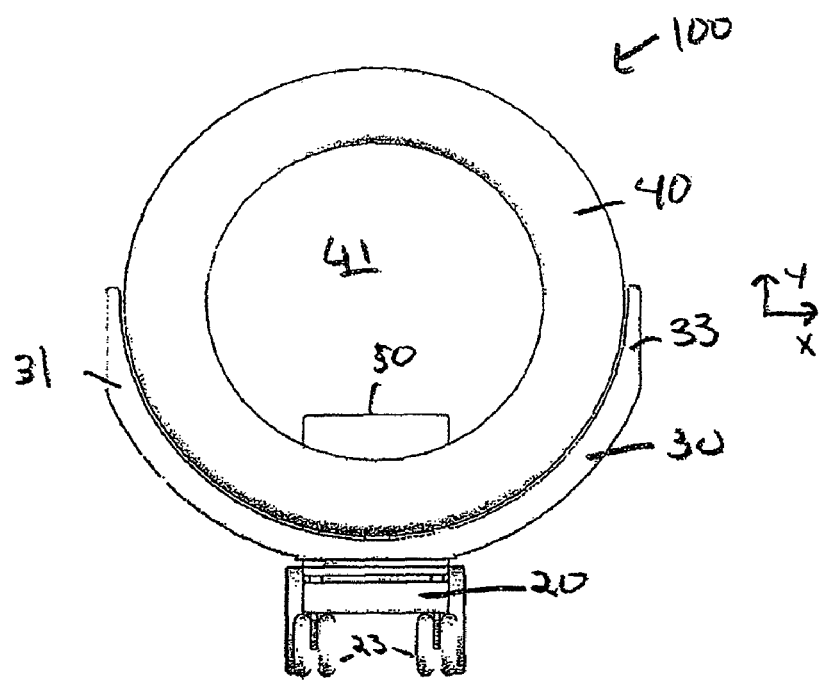
FIG. 2 is a front view of the imaging system of FIG. 1.
Figure 3:
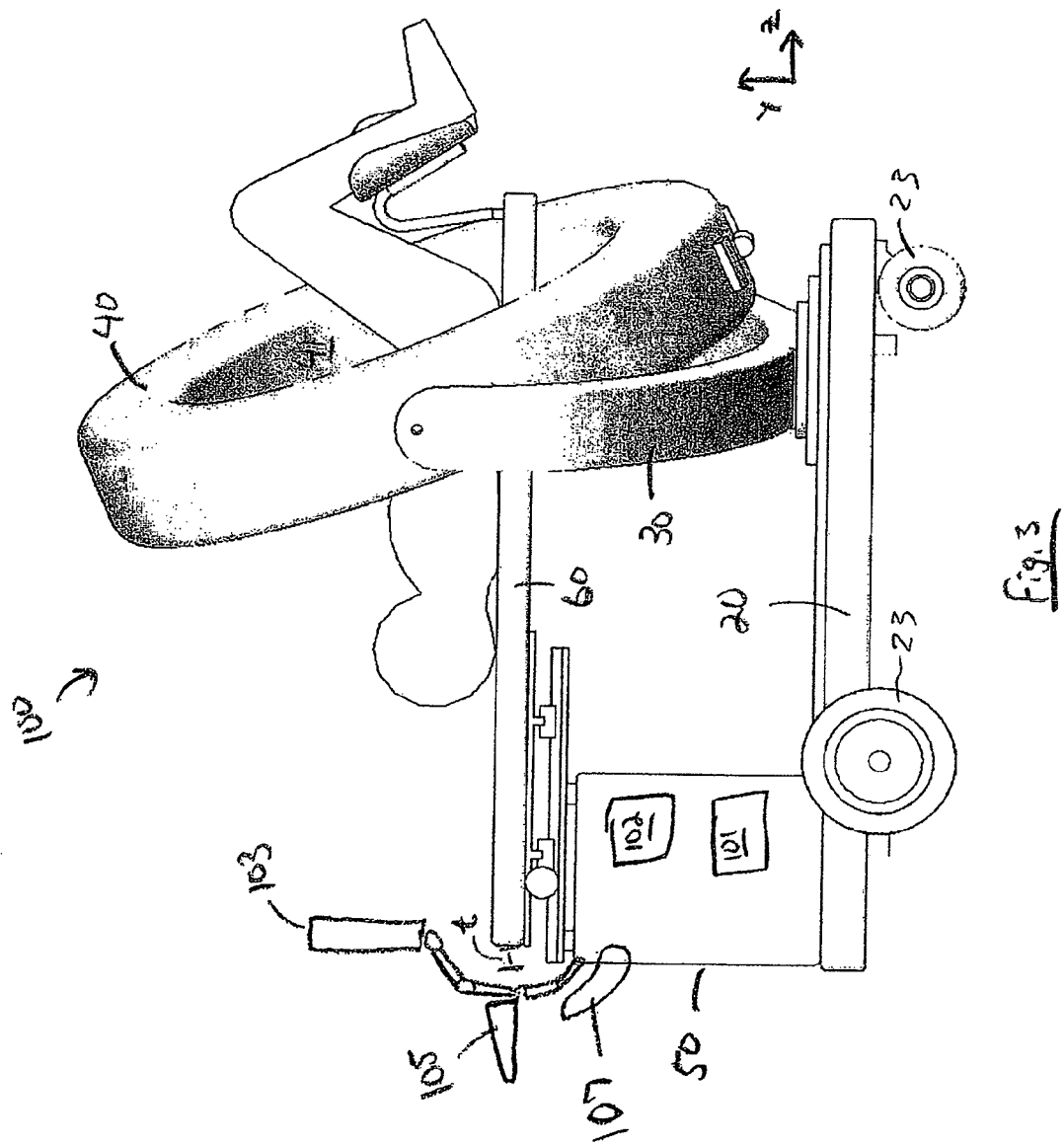
FIG. 3 illustrates an imaging system including a tabletop support supporting a patient and the gantry ring tilted and partially rotated relative to the base.

Referring to FIGS. 1-7, a mobile imaging system 100 according to one embodiment of the invention includes a mobile base 20, a gimbal support 30, a gantry ring 40, and a pedestal 50. FIGS. 1 and 2 are side and front views, respectively, of the mobile medical imaging system 100. The system 100 includes image collection devices, such as a rotatable x-ray source and detector array or stationary magnetic resonance imaging components, that are housed within the gantry ring 40. The system 100 is configured to collect imaging data, such as, for example x-ray computed tomography (CT) or magnetic resonance imaging (MRI) data, from an object located within the bore 41 of the gantry ring 40, in any manner known in the medical imaging field. As shown in FIG. 3, the pedestal 50 is adapted to support a tabletop support 60 that can be attached to the pedestal 50 in a cantilevered manner and extend out into the bore 41 of the gantry ring 40 to support a patient or other object being imaged.

The base 20 is a sturdy, generally rectilinear support platform. The base 20 may be mobile, with wheels 23 (FIGS. 1 and 2) that allow the entire imaging system 100 to be easily moved. The dimensions of the base 20 are such that the system 100 can be located in and operated comfortably in an operating room or an emergency room or an examination room. The length and width of the base 20 are preferably designed to allow the system 100 to fit through most standard-sized doorways (i.e., generally 24-36 inches wide), and to be easily transported through corridors and elevators generally found in hospitals and other health-care environments.

The gimbal support 30 (FIGS. 1-7) is a generally U-shaped support that is mounted to the top surface of base 20 and includes a pair of arms 31, 33 extending up from base. The arms 31, 33 are connected to opposite sides of gantry ring 40 so that the ring is suspended above base 20 and gimbal support 30.

Figure 4:
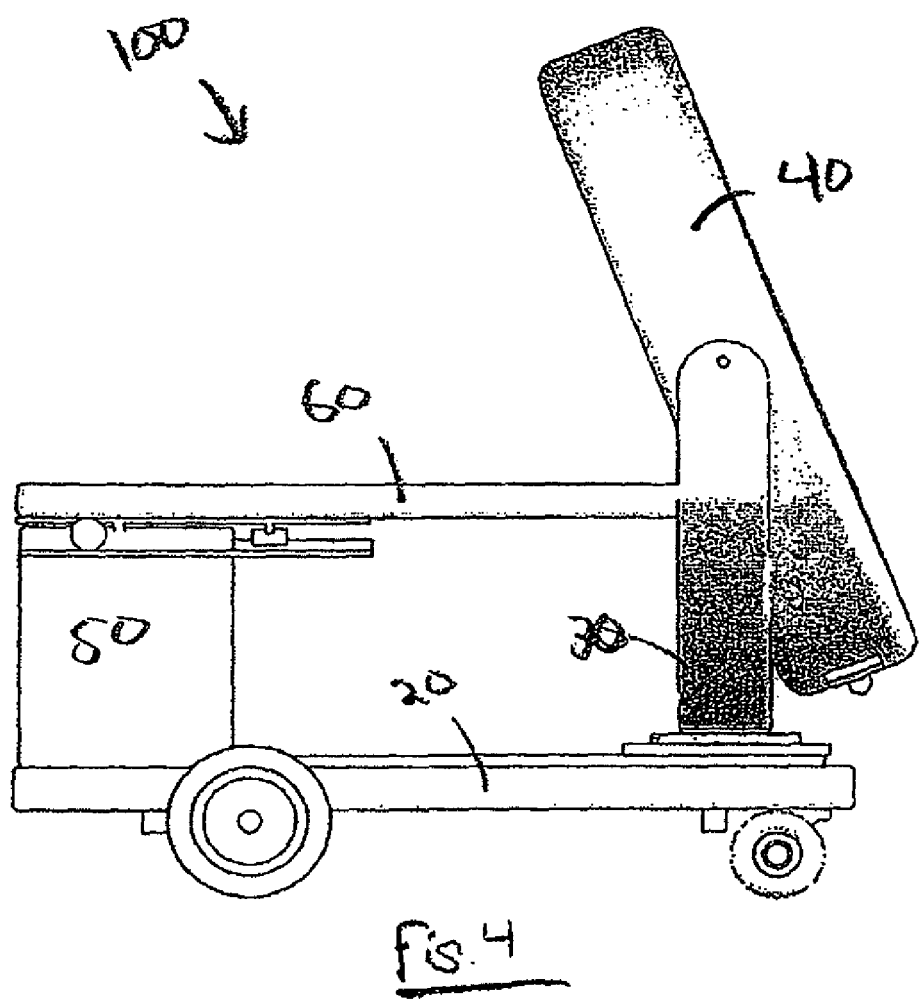
FIG. 4 is a side view of an imaging system with the gantry ring and gimbal support translated to the distal end of the base.
Figure 5:
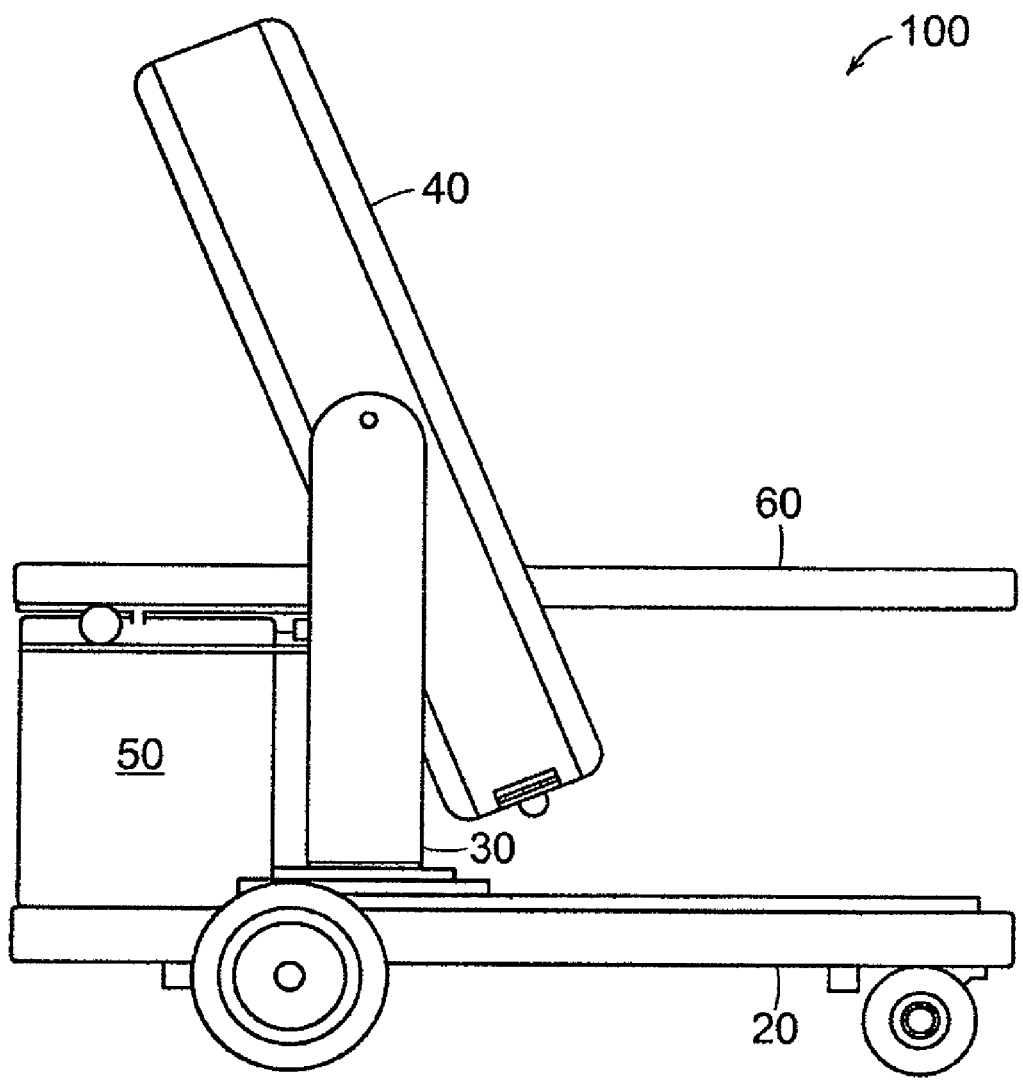
FIG. 5 is a side view of the imaging system of FIG. 4 with the gantry ring and gimbal support translated to the pedestal side of the base.

The gimbal support 30, and the gantry ring 40 to which it is attached, can translate on the base 20, as illustrated in FIGS. 4 and 5. The gimbal support 30 can translate along a substantial portion of the length of the base 20. In certain embodiments, the gimbal support 30 and gantry ring 40 can translate about 2 meters or more, which allows the gantry ring to image along any desired anatomical region of a human patient lying on a patient support. The translation distance is generally at least about 1 meter, which enables full body coverage depending on the orientation of the patient. In one embodiment, the gimbal support 30 can translate over a substantial portion of the base so that the gimbal support 30 and gantry ring 40 can be moved completely out of the way (i.e., in a "park" position) when the gantry is not in use in order to maximize access to the patient, such as for a surgical procedure.

Figure 6:
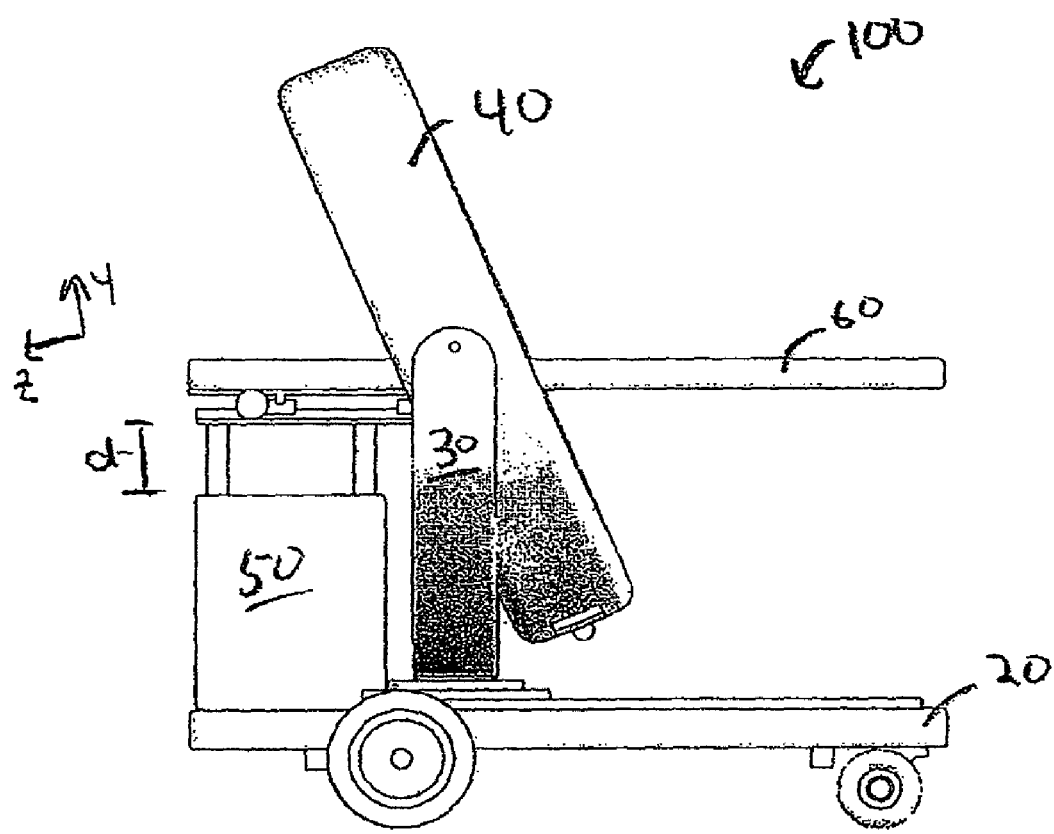
FIG. 6 is a side view of an imaging system with the tabletop support vertically displaced from the pedestal and the gantry ring tilted in a first direction with respect to the gimbal support.
Figure 7:
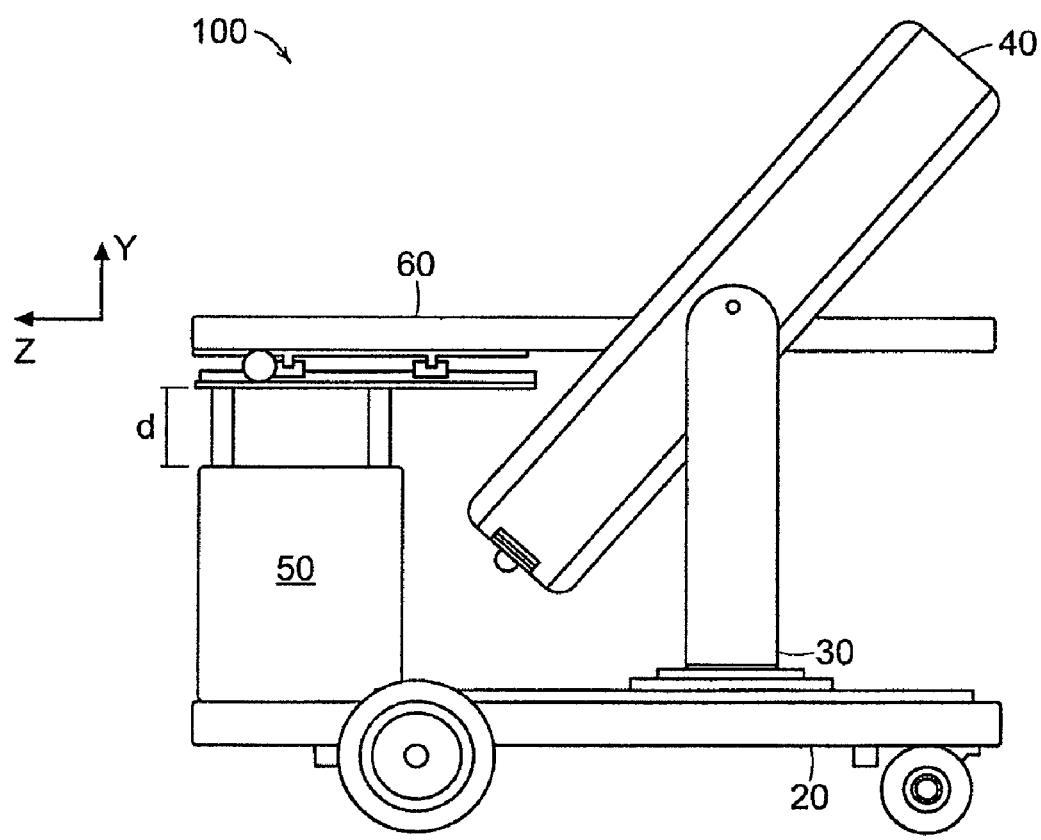
FIG. 7 is a side view of the imaging system of FIG. 6 with the gantry ring tilted in the opposite direction with respect to the gimbal support.

The gantry ring 40 can be connected to the gimbal support 30 such that the ring 40 can pivot about an axis (x-axis in FIG. 2) relative to the gimbal support 30 and the base 20. FIG. 3 illustrates the gantry ring 40 pivoted or tilted with respect to the gimbal support 30. FIGS. 6 and 7 illustrate the gantry ring 40 being tilted in two opposing directions.

The gimbal support 30 is mounted to the base 30 such that the gimbal support 30 and the gantry ring 40 can rotate about an axis (y-axis in FIGS. 1-3) relative to the base 30. This is illustrated in FIG. 3, in which the gimbal support 30 and gantry ring 40 are rotated slightly with respect to the base 20.

The pedestal 50 is mounted to the base 20. As shown in FIGS. 1-7, the pedestal 50 is mounted to the top surface of the base 20, though it could be mounted elsewhere, such as to the end of the base. The pedestal 50 can be located at or near one end of the base 20, which allows the gimbal support 30 a maximum distance over which to translate on the base.

The pedestal 50 comprises a sturdy support structure that extends generally vertically upwards from the base 20. As shown in FIGS. 3-7, the pedestal 50 is designed to securely hold a tabletop support 60 upon which the object to be imaged is supported. In one embodiment, the pedestal 50 includes a releasable locking mechanism that allows a tabletop support, or a portion thereof, to be attached to the pedestal 50 for imaging operations and removed from the pedestal 50 for storage and transport of the system 100. In addition, as discussed in greater detail below, a plurality of different tabletop supports can be attached and detached from the pedestal, where the tabletop supports are each customized for a particular application.

Generally, the pedestal 50 extends up from the base 20 to a height such that a tabletop support attached to the pedestal 50 will be approximately equal in height to the isocenter of the gantry ring. In certain embodiments, the height of the pedestal 50 can be adjusted up or down in the vertical, y-axis direction. This y-axis movement of the pedestal can be achieved by telescoping the pedestal, or by any other means known in the art, such as with a pole or ball screw. FIGS. 6 and 7, for example, illustrate the pedestal 50 and a tabletop support 60 displaced vertically by distance, d, in the y-axis. Also, in some embodiments, the pedestal 50 is configured so that a tabletop support 60 attached to the top of the pedestal 50 can move relative to the pedestal 50 and base 20. In some embodiments, the tabletop support 60 can have at least two-degrees-of-freedom relative to the pedestal 50 and base 20. The tabletop support 60 can translate along the imaging axis (z-axis) to move the tabletop support 60 towards or away from the gantry ring 40, and preferably into and out of the bore of the gantry ring 40. FIG. 3 illustrates the tabletop support 60 partially translated by distance, t, along the z-axis. In some embodiments, the tabletop support 60 can also translate along the x-axis, or into/out of the page in FIG. 3. The translation of the tabletop support 60 relative to the pedestal and base can be achieved through any known means, such as a rail and bearing system.

According to yet another aspect, the pedestal 50 can rotate with respect to the base 20 about the y-axis.

The imaging system 100 can include one or more mechanical actuators, as are known in the art, to control and effect the above-described motions—i.e., the tilt motion of the gantry ring relative to the gimbal support, the translation and rotation of the gimbal support relative to the base, the up-down motion of the pedestal, the z-axis and x-axis translation of the tabletop support, and the y-axis rotation of the pedestal. All of these respective motions can be controlled by a central computerized system controller 102 (FIG. 3). The system controller 102 can be included on the system, such as housed inside the pedestal 50, as shown in FIG. 3. In other embodiments, the system controller is located off the system 100, such as in a mobile cart, and may comprise a general purpose computer programmed to provide the desired control functions and user interface, and is in electrical communication with the system 100, such as via a cable or wireless link. The control system 102 can also control the operation of the imaging device(s) on the gantry ring 40, as discussed further below.

It will be understood that the above-described movements of the gantry ring 40, gimbal support 30, pedestal 50 and tabletop support 60 are not required in all embodiments, and that some or all of these movements, if provided, can be made manually by an operator rather than by a motorized system. The advantages of the various movements described above is that they can aid in the loading and unloading of objects to be imaged onto and off of the imaging system, they allow for fine-tuning of the positioning of the object for imaging applications, and they enable a wide variety of imaging angles and scanning operations.

Other components of the system 100 include a power supply 101, which can be a rechargeable battery-based power supply, a user display 103 and a user input system 105 for controlling the operation of the system. In the embodiment of FIG. 3, these components are shown on the imaging system 100, for example, housed within or attached to the pedestal 50, though it will be understood that some or all of these components could be located off the system 100, such as on a separate mobile cart.

The imaging system 100 can also include a motor that is geared into the wheels 23 to propel the system 100 across a floor. The system 100 can also include a steering mechanism, such as handle 107. The handle 107 in this embodiment is shown attached to pedestal 50, though it could be located elsewhere on the system, including on the gimbal support 30.

Figure 8:
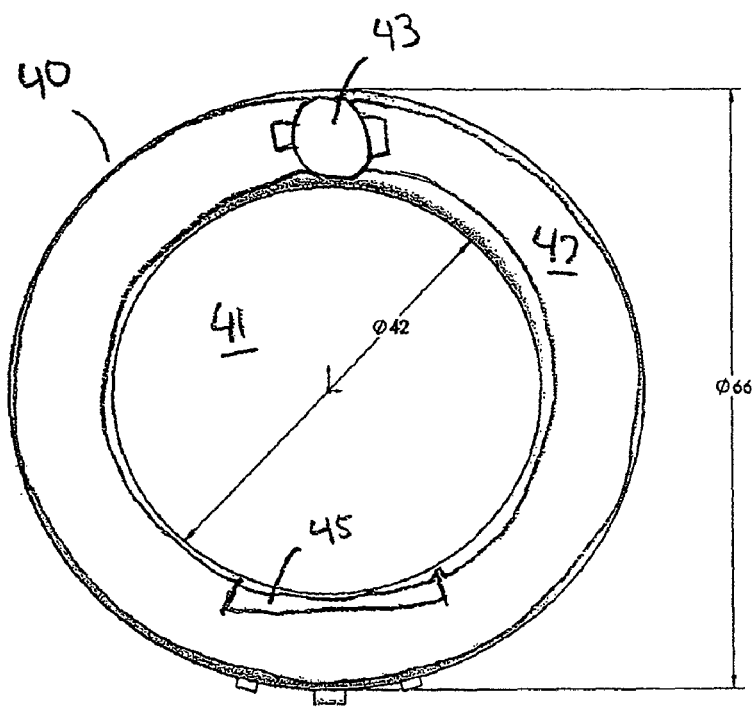
FIG. 8 is a front cross-sectional view of a gantry ring having an x-ray source and an x-ray detector array on a rotor.

Turning now to FIG. 8, the gantry ring 40 is shown in a head-on, cross-sectional view to illustrate the imaging components inside the gantry ring 40, according to one embodiment of the invention. As shown in FIG. 8, the gantry ring 40 comprises a generally O-shaped housing that surrounds and defines an inner bore 41. Inside the housing are imaging components, including in this embodiment, an x-ray source 43 and an x-ray detector array 45, as are known in the field of computed tomography. The source 43 and the detector 45 are positioned on opposite sides of the ring. In certain embodiments, the source and detector rotate around the interior of the housing in coordination with each another to perform an imaging scan of an object located within the bore 41. In the embodiment of FIG. 8, both the source and the detector are mounted to a rotor 47, and the rotor 47 is rotated within the gantry ring 40 to effect the x-ray scanning. A motor and drive mechanism can controllably rotate the rotor within the ring 40, as is known in the art. Electrical signals, including for example, electrical power and control signals to the imaging equipment, and data signals from the imaging equipment, can be passed between the rotor 47 and the rest of the imaging system via a slip ring or cable system, or via any manner known in the art. In some embodiments, at least some of the signals can be passed via a wireless link between the control system and the imaging equipment on the rotor. Also, in some embodiments, all or a portion of the electrical power for the imaging equipment can be provided by a power supply located on the rotor 47, such as a rechargeable battery-based power supply.

The outer shell or housing of the gantry ring 40 can be comprised of any sufficiently rigid and strong material, such as high-strength plastic, metal, carbon fiber and the like. The outer diameter of the ring 40 can be relatively small to improve the portability of the system 100. In a preferred embodiment, the outer diameter of the ring 40 is less than about 70 inches, and in one embodiment is about 66 inches. In addition, the interior diameter of the ring 40, or bore 41 diameter, can be sufficiently large to allow for the widest variety of patient support tables to fit inside the bore, and to facilitate access to a subject located inside the bore. In one embodiment, the bore diameter of the gantry ring 40 is greater than about 38 inches, and can be between about 40 and 50 inches. In one exemplary embodiment, the bore has a diameter of about 42 inches.

Figure 9:
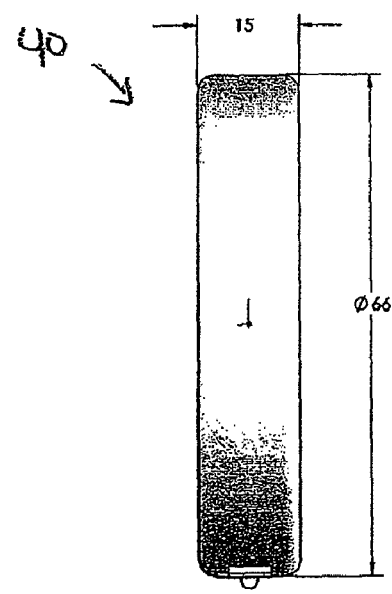
FIG. 9 is a side view of the gantry ring.

FIG. 9 is a side view of the gantry ring 40. As can be seen from FIG. 9, the gantry ring 40 generally has a narrow profile which is consistent with the portability of the system. This can also help facilitate the mobility of the system, such as in a transport mode, as discussed below. In one embodiment, the width of the gantry ring 40 is less than about 17 inches, and can be about 15 inches or less.

Figure 10A:
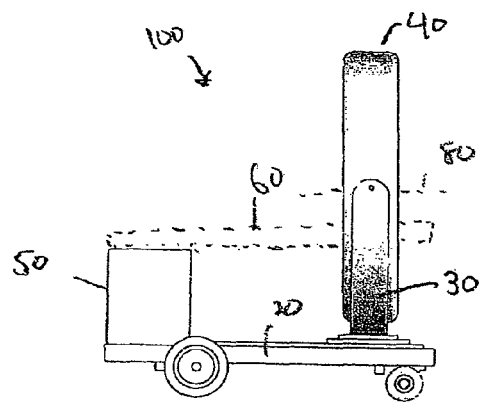
FIGS. 10A and 10B are side and top views, respectively, of an imaging system of the invention in an imaging position.
Figure 10B:
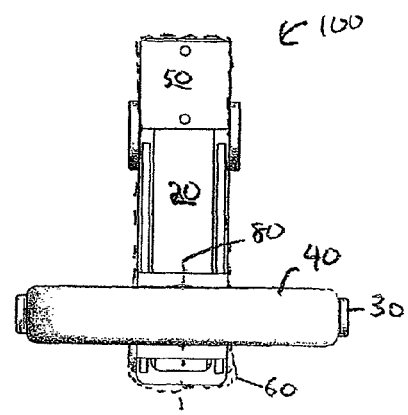
Figure 11A:
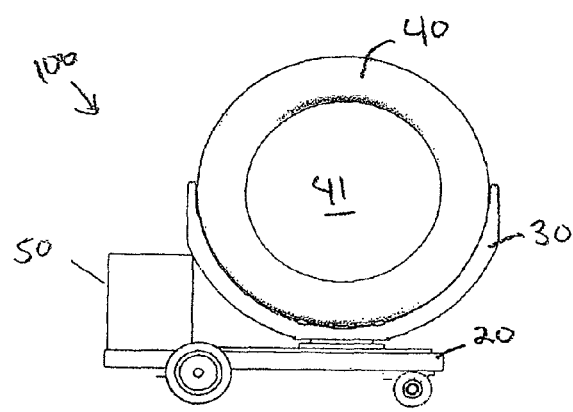
FIGS. 11A and 11B are side and top views, respectively, of the imaging system of FIGS. 10A and 10B in a transport position.
Figure 11B:
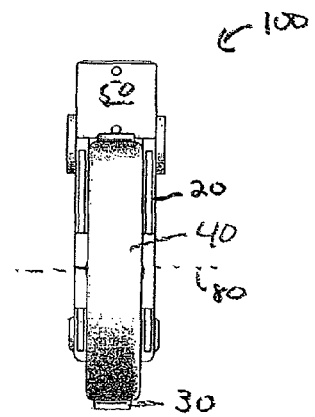

Turning now to FIGS. 10A, 10B, 11A and 11B, the imaging system 100 is illustrated in an imaging position and a transport position. FIGS. 10A and 10B are side and top views, respectively, of the imaging system 100 in an imaging position. In this position, a tabletop support 60, shown in phantom, is mounted to the pedestal 50 and extends from the pedestal 50 in a cantilevered manner in the direction of the gantry ring 40. The gantry ring 40 is oriented generally perpendicular to the length of the base 20, and the bore 41 imaging axis 80 faces generally towards the pedestal 50 and parallel to the length of the base 20. At least a portion of the tabletop support 60 extends inside the bore 41, such that an object on the tabletop support 60 can be imaged using the imaging equipment in the gantry ring 40. As previously discussed, the gantry ring 40 can translate along the length of the base 20 to obtain images of the object along the imaging axis 80. In FIGS. 11A and 11B, the imaging system 100 is in a transport position. The tabletop support 60 has been removed from the imaging area. In the transport position, the gantry ring 40 is oriented generally parallel to, or in-line with, the length of the base 20. The bore 41 imaging axis 80 is now generally perpendicular to the length of the base 20. The profile of the system 100 is thus dramatically reduced in comparison to the imaging position, such that the system in a transport position is typically only as wide as the width of the base 20 and pedestal 50. This advantageously allows the system 100 to be more easily transported through narrow doors and hallways. The imaging system 100 can easily switch between an imaging position and a transport position, and vice versa, by rotating the gantry ring 40 with respect to the base 20. This can be done by rotating the gimbal support 30, which carries the gantry ring 40, on the base 20. The gantry ring 40 can be rotatable with respect to the base 20 at least about 90 degrees to switch between a transport position and an imaging position. In certain embodiments, the gantry 40 can rotate more that 90 degrees, including, for example, 180 degrees, 270 degrees, 360 degrees or more, relative to the base 20. Further, the rotation of the gantry ring 40 with respect to the base can be bi-directional (i.e., both clockwise and counterclockwise).

As seen in FIGS. 11A and 11B, the tabletop support 60 used for imaging applications is at least partially removed from the imaging area when the system 100 is in a transport mode. This is required in order to provide sufficient clearance for the gantry ring 40 to rotate from an imaging position to the narrower transport configuration. In certain embodiments, the tabletop support 60 is removed from the imaging area by detaching the entire tabletop support 60, or a portion thereof, from the pedestal 50. In other embodiments, the tabletop support 60 can be removed from the imaging area by other means, such as by sliding the tabletop support out of the imaging area, folding the tabletop support over to provide sufficient clearance for the gantry ring, by retracting a portion of the tabletop support, such as by an accordion- or telescoping-action, or by a combination of the above.

Figure 12:
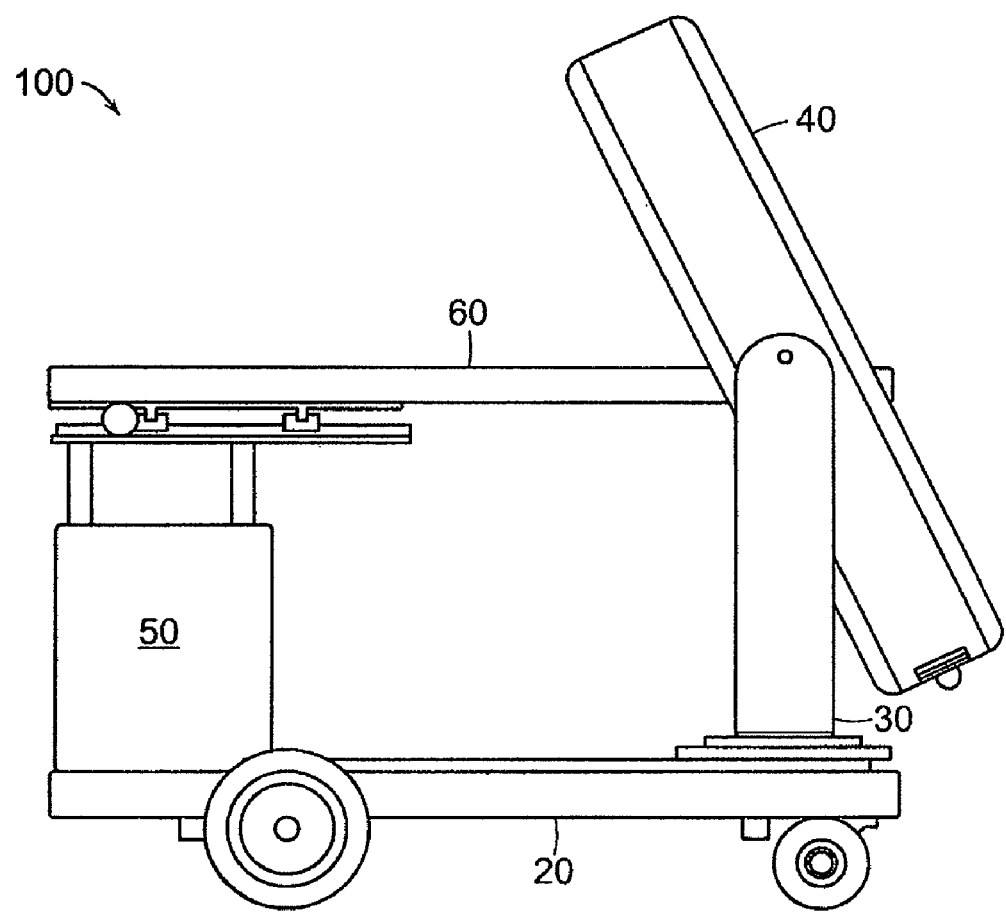
FIG. 12 is a side view of an imaging system with a flat operating tabletop support mounted on the pedestal.
Figure 13:
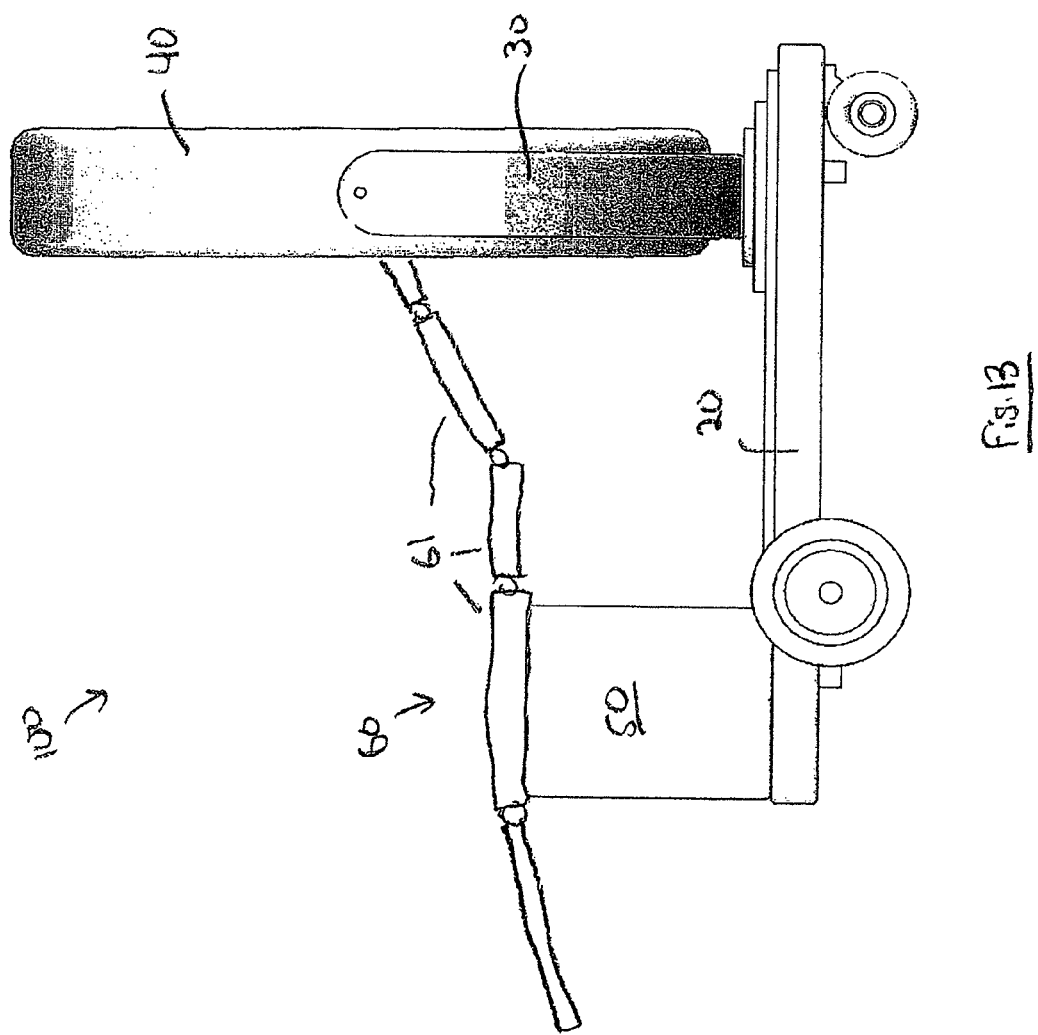
FIG. 13 is a side view of an imaging system with a modular, sectional tabletop support mounted on the pedestal.
Figure 14:
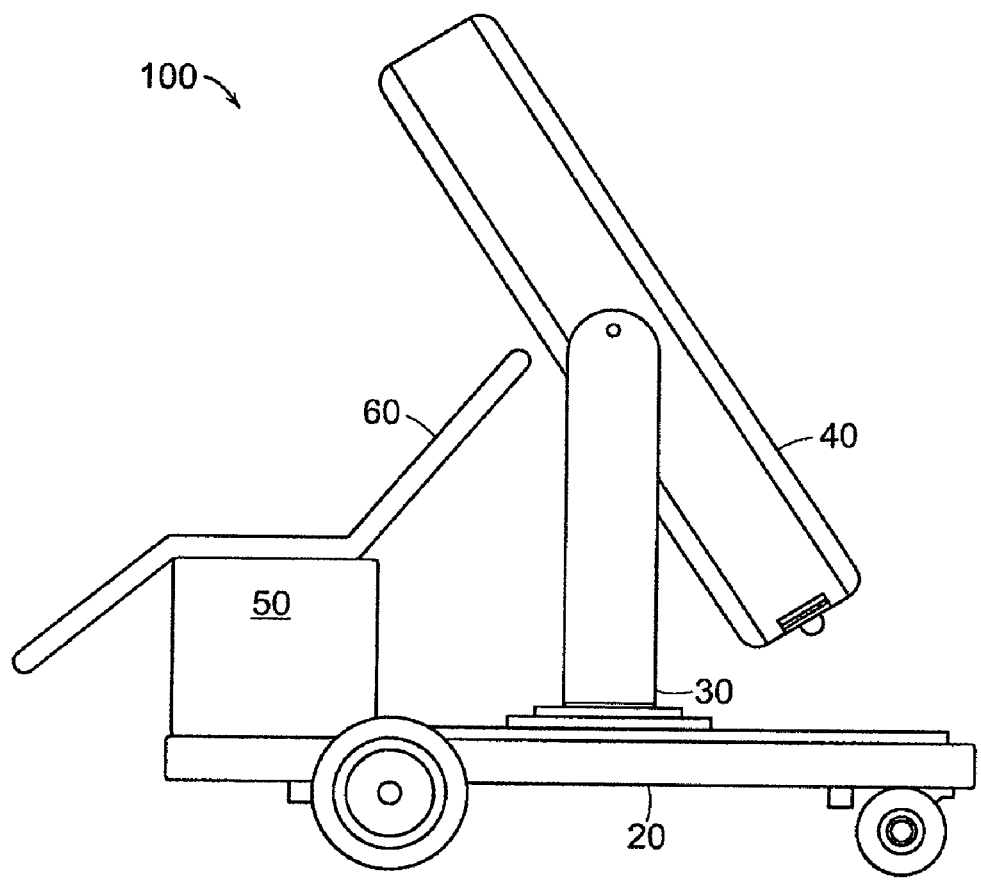
FIG. 14 is a side view of an imaging system with a tabletop support in the form of a chair for imaging a seated patient.

In one embodiment, the imaging system 100 is configured to receive a plurality of different tabletop support 60 structures, wherein different tabletop supports 60 are procedure-specific and customized to particular applications. The tabletop supports 60 can be conventional radiological tables, and can also comprise true surgical and trauma tables. The tabletop supports 60 can also comprise chairs to permit imaging of a patient in a seated position. FIGS. 12-14 illustrate various examples of tabletop supports 60 that can be attached to the pedestal 50 for an imaging operation. FIG. 12 illustrates a flat, operating tabletop support 60 that is mounted to the pedestal 50 and cantilevered into the imaging area. The tabletop support 60 can be wholly or partially radiolucent. FIG. 13 illustrates a modular tabletop support 60 that includes sections 61 that can be added to and removed from the tabletop support, and oriented relative to one another, to provide a wide variety of patient orientations. FIG. 14 illustrates a tabletop support 60 in the form of a chair that allows imaging of a seated patient. This configuration permits the imaging of a patient's chest area while in a seated position. The chair can be rotatable on the pedestal 50 at least 90 degrees, and in some cases 180 degrees or more, from an imaging position to a position that allows greater access to the patient by medical professionals.

Figure 15A:
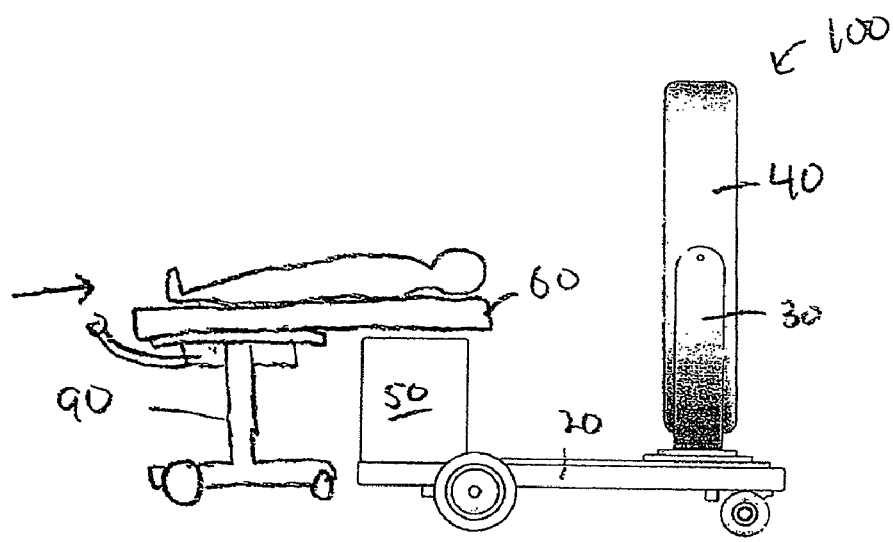
FIGS. 15A-15C illustrate a patient tabletop support that is transported to an imaging system on a mobile cart for imaging a patient and then removed from the imaging system using the mobile cart.
Figure 15B:
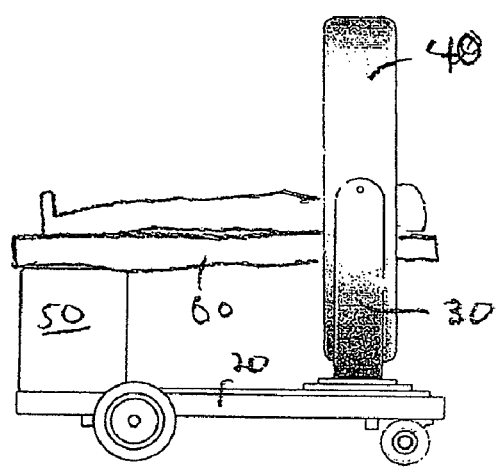
Figure 15C:
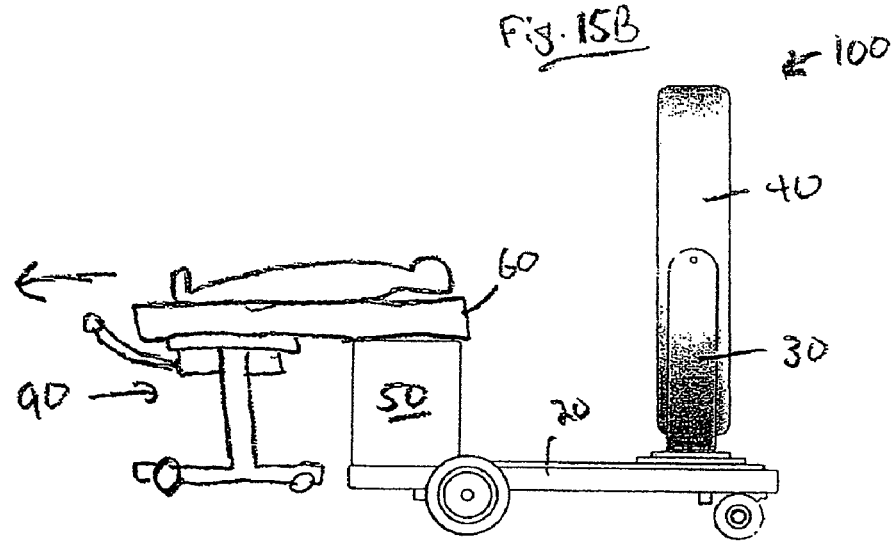

In one embodiment, as shown in FIGS. 15A-15C, the tabletop support 60 is transported to the imaging system 100 on a mobile cart 90. A patient can be pre-positioned and prepped on the cart 90 and then moved to the imaging system 100. The entire tabletop support 60 can then be moved over and locked onto the top of pedestal 50 with the patient already in position for imaging and/or a medical procedure. As shown in FIG. 15B, the cart 90 is released from the tabletop support 60, and the tabletop support 60 is positioned inside the gantry ring 40 for an imaging application. The positioning of the tabletop support 60 within the system 100 can include any or all of the tabletop support movements previously described, including, for example, the z-axis and x-axis tabletop translation relative to the pedestal 50, the up/down y-axis motion of the pedestal 50, the y-axis rotation of the pedestal 50, as well as a multi-axis tilt motion of the tabletop relative to the pedestal. Following the imaging procedure, the tabletop support 60, along with the imaged subject, can be unlocked from the pedestal 50 and removed from the imaging system 100 via the cart 90, as shown in FIG. 15C. Alternatively, the tabletop support 60 can remain attached to the pedestal 50 while a medical procedure is performed on the imaged subject. When an imaging subject is undergoing a procedure, the gimbal support 30 and the gantry ring 40 can be translated to either the furthest distal or the furthest proximal position on the base 20, in a "park" mode, to provide the greatest amount of access to the patient by medical professionals. In one embodiment, the gimbal support 30 and gantry ring 40 can translate along substantially the full length of the base 20 between the pedestal 50 and the distal end of the base, to maximize both the area over which the subject can be imaged and the area in which the imaging subject can be freely accessed when not being imaged.

It will be understood that virtually any type of tabletop support structure can be used in the present imaging system. For example, the present imaging system can utilize medical tables, and related accessories, of the type described in the JUPITER system brochure (11/2008) from TRUMPF Medezin Systeme GmbH & Co. KG of Puchheim, Germany, the entire contents of which are incorporated herein by reference. Furthermore, although the present embodiments illustrate tabletop supports that can be used for medical imaging of human patients, it will be understood that the present invention encompasses any suitable tabletop support structure, including those designed for or suitable to support non-human subjects and non-living objects and materials.

Figure 16:
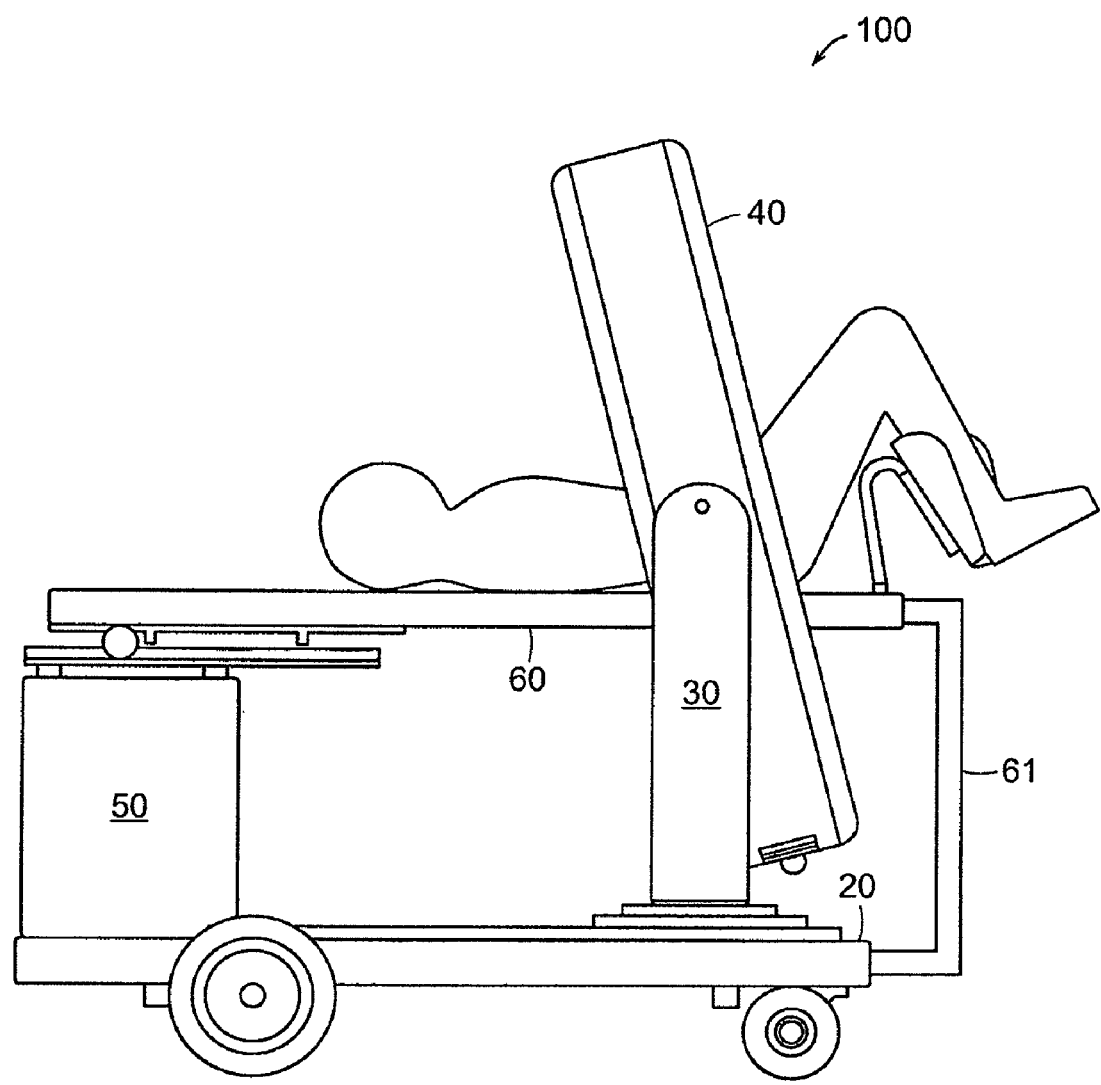
FIG. 16 is a side view of an imaging system having a rod to reinforce the cantilevered end of the tabletop support.

Turning now to FIG. 16, an embodiment of the invention is illustrated that includes a cantilevered tabletop support 60 with a pole 61 to provide additional support for the distal, cantilevered end of the tabletop support 60. The pole 61 can be attached to the base 20, and in certain embodiments, the pole 61 can extend from and retract wholly or partially into the base 20, such as in a telescoping manner.

Figure 17:
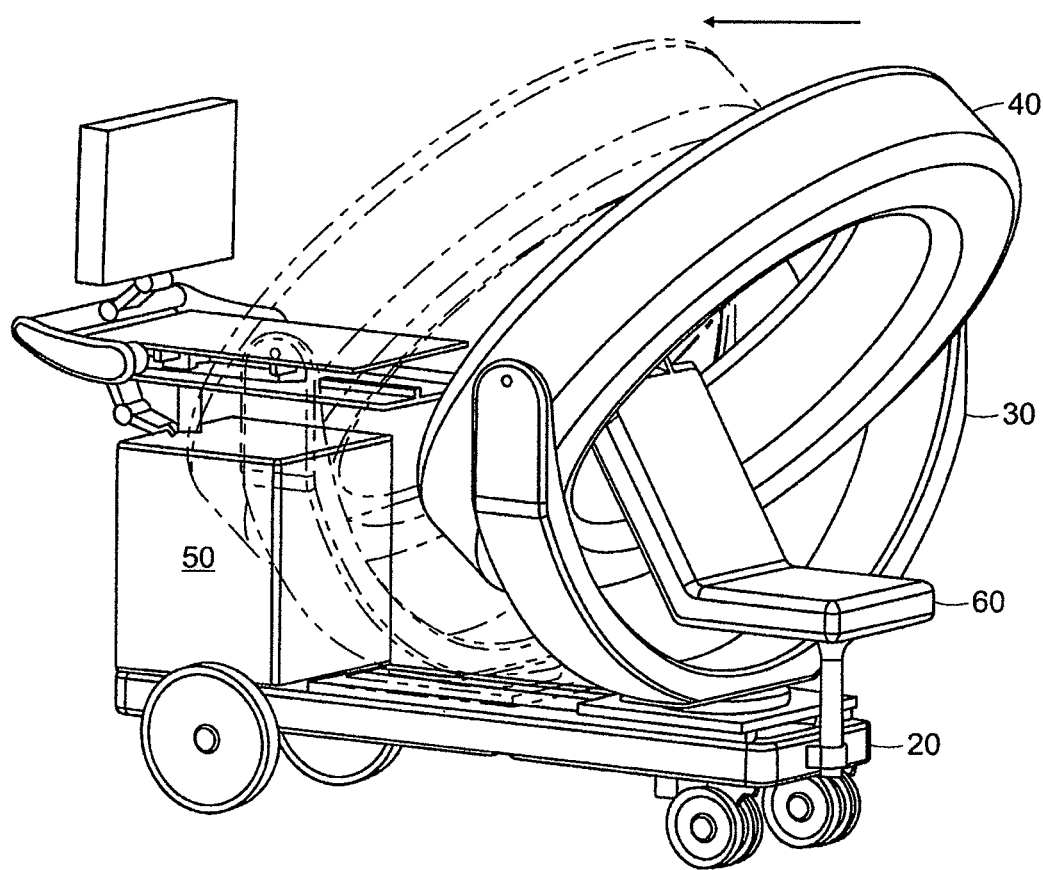
FIG. 17 is a front perspective view of an imaging system having a chair support mounted to the distal end of the base.

FIG. 17 illustrates an embodiment of the invention in which a tabletop support 60 is mounted directly to the distal end of the base 20. In this embodiment, the tabletop support 60 comprises a chair that enables imaging of a patient in a sitting position.

Figure 18:
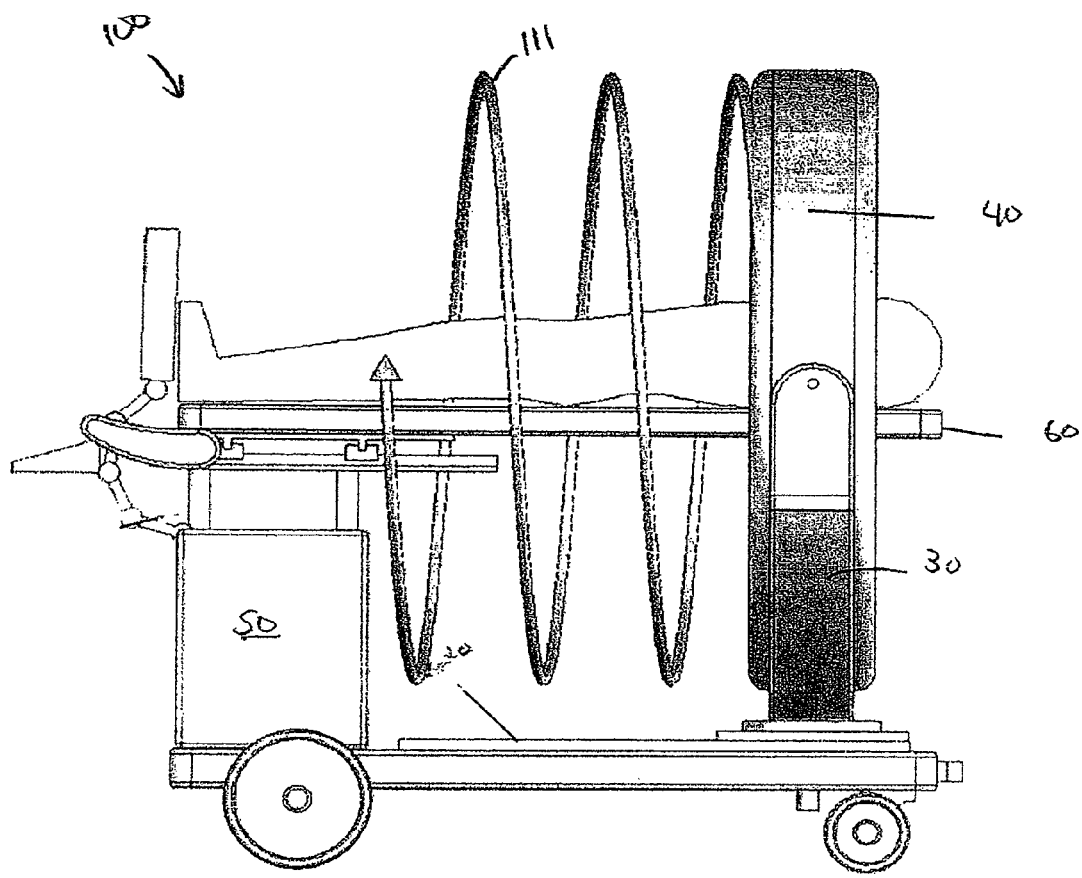
FIG. 18 illustrates an imaging system of the invention performing a helical scanning procedure.

FIG. 18 illustrates a helical scanning imaging application of the present invention. The imaging equipment (e.g., x-ray source and detector) rotate around the interior of the gantry ring 40 to obtain imaging data, while the gantry ring 40 and gimbal support 30 simultaneously translate along the base 20. The arrow 111 indicates the path of the imaging equipment around the patient in a helical scan. The present imaging system is thus able to obtain true helical scan x-ray CT images, as are well-known in the art.

Figure 19:
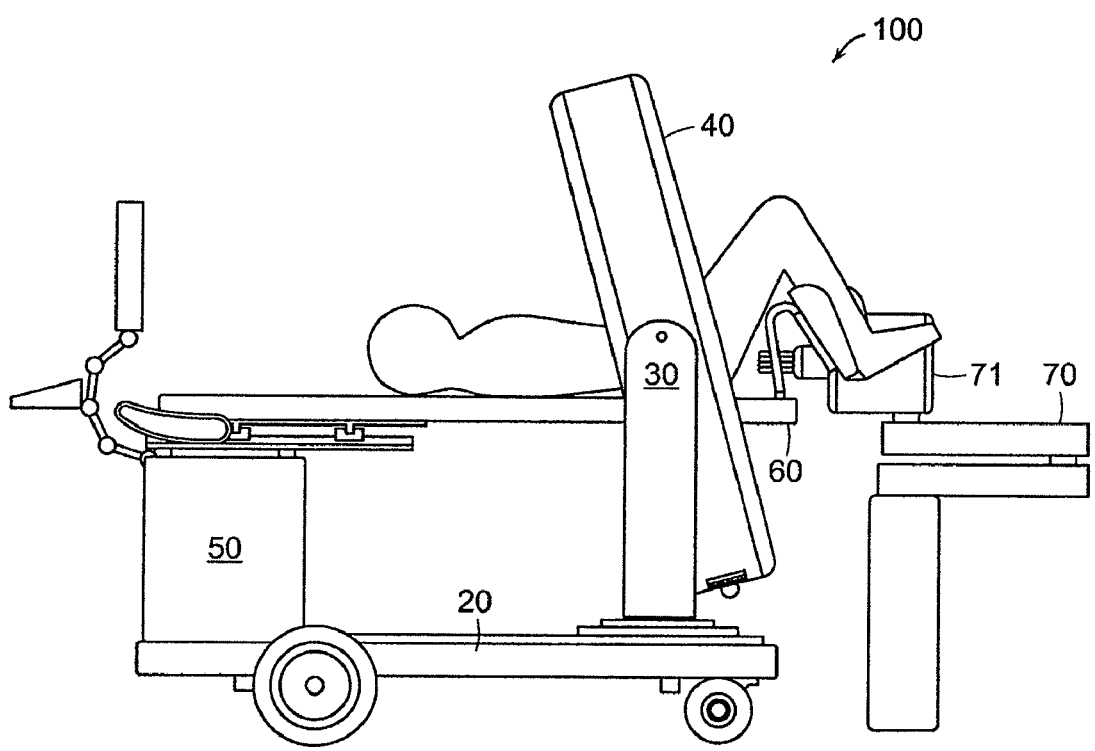
FIG. 19 illustrates an imaging system of the invention and a specialized support with a medical device for performing a procedure on a patient.

FIG. 19 is a side view of an embodiment of the present imaging system 100 in which the gantry ring 40 is tilted on the gimbal support 30. A patient is supported partially on tabletop support 60 and partially on a specialized support 70 that enables the patient to be imaged in a stirrup position. The specialized support 70 further includes a medical device 71 for performing a medical procedure on the patient. The present system thus enables medical personnel to obtain high-quality images of the patient, including 3D tomographic reconstructions, while performing a medical procedure on the patient. The present system is particularly advantageous, for example, for performing brachytherapy.

It will be understood that the imaging systems described herein may be constructed of any sufficiently rigid and strong materials such as high-strength plastic, metal, carbon fiber and the like, as well as combinations of the same.

The advantages of the present invention include, without limitation, that the present imaging systems in certain embodiments are portable and exceedingly easy to transport. Embodiments of present imaging system are easy to move into a hospital, office or elevator because the device is relatively small and lightweight. Moving such a device typically requires only a single person, even when taking the system up or down a ramp. Further, certain embodiments of the system can pass through most standard doorways without requiring any widening of the doorways. Further, the system can easily be moved from spot to spot once inside a room.

In one aspect, the present invention is an imaging system in which an imaging gantry ring can tilt, rotate or translate along a mobile base with a detachable or movable patient tabletop support, thus allowing the apparatus to be easily transportable. The rotation and tilt axes of the gantry ring permits the gantry ring to be oriented generally perpendicular to the mobile base, allowing a cantilevered tabletop support to pass through the center of the gantry ring in certain imaging modes, and further allows the gantry ring to be rotated generally in-line with the mobile base in a transport mode, thus allowing the apparatus to be as narrow as possible to pass through hallways, corridors or elevators.

Those of ordinary skill will understand and appreciate the existence of variations, combinations, and equivalents of the specific embodiments, methods, and examples disclosed herein. The invention should therefore not be limited except by the scope and spirit of the appended claims.

What is claimed is:

1. A medical imaging system, comprising:
   a base having a top surface, a first end and a second end;
   a pedestal connected to the base and positioned adjacent to the first end of the base, the pedestal extending in a vertical direction above the top surface of the base and configured to accept a plurality of interchangeable procedure-specific tabletop supports, and the pedestal is rotatable about an axis extending generally normal to the top surface of the base; and
   a gantry ring having a bore and an image collection apparatus, the gantry ring coupled to the base and positioned above the top surface of base, the gantry ring configured to translate along a length of the base between a first position adjacent to the pedestal to a second position adjacent to the second end of the base, the gantry ring further configured to rotate at least about 90 degrees with respect to an axis extending generally normal to the top surface of the base.

2. The medical imaging system of claim 1, wherein the base comprises a mobile base having one or more wheels attached to the base.

3. The medical imaging system of claim 1, wherein the gantry ring translates and rotates by the translation and rotation of the gimbal support relative to the base.

4. The medical imaging system of claim 1, wherein the gimbal support comprises a generally U-shaped support having arms extending upwards from the base and connecting to opposite sides of the gantry ring.

5. The medical imaging system of claim 4, wherein the gantry ring is pivotable with respect to the gimbal support to tilt the gantry ring relative to the gimbal support and the base.

6. The medical imaging system of claim 1, wherein the image collection apparatus comprises an x-ray source and an x-ray detector array.

7. The medical imaging system of claim 6, wherein the x-ray source and the x-ray detector rotate 360 degrees around the interior of the gantry ring to obtain imaging data of an object positioned within the bore.

8. The medical imaging system of claim 7, wherein the x-ray source and x-ray detector are mounted to a rotor, the rotor rotating around the interior of the gantry ring.

9. The medical imaging system of claim 1, further comprising a tabletop support mounted to and disposed above the pedestal, the tabletop support extending at least partially into the bore of the gantry ring.

10. The medical imaging system of claim 9, wherein the tabletop support is detachable from the pedestal.

11. The medical imaging system of claim 9, wherein the tabletop support comprises a surgical or trauma table.

12. The medical imaging system of claim 9, wherein the tabletop support comprises a chair for imaging of a seated patient.

13. The medical imaging system of claim 9, wherein the tabletop support comprises a plurality of modular sections that can be added to and removed from the tabletop support to modify the configuration of the tabletop support.

14. The medical imaging system of claim 1, wherein the pedestal is adapted to support any one of a plurality of interchangeable tabletop supports.

15. The medical imaging system of claim 1, wherein the base has a length and a width, and the gantry translates along the length of the base.

16. The medical imaging system of claim 15, wherein the pedestal is mounted to the base at or near a first end of the base, and the gantry ring translates over substantially the entire length of the base from the pedestal to the second end of the base.

17. The medical imaging system of claim 15, wherein the gantry ring translates at least about one meter along the length of the base.

18. The medical imaging system of claim 1, wherein the gantry ring has an inner bore diameter that is greater than about 38 inches.

19. The medical imaging system of claim 18, wherein the bore diameter is between about 40 and 50 inches.

20. The medical imaging system of claim 1, wherein the outer diameter of the gantry ring is less than about 70 inches.

21. The medical imaging system of claim 1, wherein the gantry ring has a width of about 17 inches or less.

22. The medical imaging system of claim 1, wherein the gantry ring rotates about said axis between an imaging position, wherein the bore of the gantry ring is faced generally in the direction of the pedestal, and a transport position, wherein the bore is faced generally perpendicular to the pedestal.

23. The medical imaging system of claim 22, wherein the system has a first width when the gantry ring is in an imaging position and a second width when the gantry ring is in a transport position, the second width being less than the first width.

24. The medical imaging system of claim 1, wherein the height of the pedestal above the top surface of the base is adjustable.

25. The medical imaging system of claim 1, wherein the pedestal is configured to receive and secure a tabletop support on a top surface of the pedestal, and the tabletop support translates in at least one direction relative to the pedestal and base.

26. The medical imaging system of claim 1, further comprising a releasable locking mechanism for securing a tabletop support on a top surface of the pedestal.

27. The medical imaging system of claim 1, further comprising at least one actuator for translating and rotating the gantry ring on the base.

28. The medical imaging system of claim 1, further comprising a control system for controlling the operation of the image collection equipment and the translation and rotation of the gantry.

29. The medical imaging system of claim 1, further comprising a tabletop support mounted directly to the base, the tabletop support extending at least partially into the bore of the gantry ring.

30. The medical imaging system of claim 1, wherein the tabletop support comprises a chair.

31. The medical imaging system of claim 1, further comprising a retractable support element that extends upwards from the base to support a cantilevered end of a tabletop support that is mounted to the pedestal.

32. The medical imaging system of claim 1, wherein the system comprises a mobile system and further comprises a drive mechanism for propelling the system.

33. The medical imaging system of claim 1, wherein the system comprises a computed tomography (CT) imaging system.

34. The medical imaging system of claim 1, wherein the system comprises a magnetic resonance imaging (MRI) system.

35. The medical imaging system of claim 1, wherein the gantry ring has an inner bore diameter that is greater than 38 inches, an outer diameter that is less than 70 inches, and a with of less than 17 inches.

36. The medical imaging system of claim 35, wherein the inner bore diameter is between about 40 and 50 inches, and the width of the gantry ring less than about 15 inches.

37. The medical imaging system of claim 1, further comprising:
 a gimbal support connected to the base, the gantry ring being attached to the gimbal support and suspended above the top surface of the base.

38. A method of imaging an object with a medical imaging system having a base with a top surface, a first end and a second end, a pedestal connected to the base and positioned adjacent to the first end of the base, a gantry ring having a bore and an image collection apparatus, the gantry ring coupled to the base and positioned above the top surface of the base, the method comprising:
 rotating the gantry ring about an axis extending generally normal to the top surface of the base, the gantry ring rotating at least about 90 degrees from a transport position to an imaging position;
 transporting a tabletop support to the pedestal;
 securing the tabletop support on the pedestal, the tabletop support extending from the pedestal into an imaging area that is above the base and in the direction of the gantry ring, an object to be imaged being positioned on the tabletop support;
 adjusting the relative positions of the tabletop support and the gantry ring until a region of interest is located inside the bore of the gantry ring;
 translating the gantry ring in a first direction relative to the base;
 obtaining image data of the object using the image collection apparatus on the gantry ring; and
 removing the tabletop support from the pedestal.

39. The method of claim 38, further comprising:
 removing at least a portion of the tabletop support from the imaging area; and
 rotating the gantry ring at least about 90 degrees from the imaging position to the transport position.

40. The method of claim 38, wherein the image collection apparatus comprises an x-ray source and x-ray detector array.

41. The method of claim 40, wherein obtaining image data comprises rotating at least one of the x-ray source and the x-ray detector array around the interior of the gantry ring.

42. The method of claim 41, further comprising translating the gantry while at least one of the x-ray source and x-ray detector rotate in the gantry ring to perform a helical scan.

43. The method of claim 38, further comprising:
 removing the tabletop support from the pedestal and providing a second tabletop support for a second imaging operation.

44. The method of claim 43, wherein at least one of the tabletop supports comprises a chair.

45. The method of claim 43, wherein at leas one of the first and second tabletop supports comprises a procedure-specific tabletop support.

46. The method of claim 38, further comprising transporting the imaging system when the gantry ring is in the transport position.

47. The method of claim 46, wherein the imaging system is transported on wheels attached to the base.

48. The method of claim 38, further comprising:
 positioning a patient on the tabletop support;
 transporting the patient on the tabletop support to the imaging system; and
 removing the patient and the tabletop support from the system after obtaining image data from the patient.

49. The method of claim 38, further comprising:
 rotating the pedestal and tabletop support relative to the base to bring the tabletop support into and out of the imaging area.

50. The method of claim 38, further comprising:
 translating the gantry to at least one of a first position, proximate the pedestal, and a second position, proximate the second end of the base, when not obtaining images to provide access to the object being imaged.

51. The method of claim 38, wherein the gantry ring has an inner bore diameter that is greater than 38 inches, an outer diameter that is less than 70 inches, and a with of less than 17 inches.

52. The method of claim 51, wherein the inner bore diameter is between about 40 and 50 inches, and the width of the gantry ring less than about 15 inches.

53. The method of claim 38, wherein the medical imaging system comprises a gimbal support connected to the base, and a the gantry ring is attached to the gimbal support and suspended above the top surface of the base.

54. The method of claim 53, wherein rotating the gantry ring comprises rotating the gimbal support with respect to the base.

55. The method of claim 53, wherein translating the gantry ring comprises translating the gimbal support with respect to the base.

56. The method of claim 53, wherein the object being imaged comprises a human or animal patient.

57. The method of claim 56, further comprising performing a medical procedure on the patient while the patient is positioned on the tabletop support.

58. The method of claim 57, further comprising translating the gantry ring to provide access to the patient for a medical procedure.

59. The method of claim 56, wherein the tabletop support is transported on a mobile cart.

60. The method of claim 57, wherein the medical procedure comprises brachytherapy.

61. A medical imaging system, comprising:
 a base having a top surface, a first end and a second end;
 a pedestal connected to the base and positioned adjacent to the first end of the base, the pedestal extending in a vertical direction above the top surface of the base and configured to accept a plurality of interchangeable procedure-specific tabletop supports, the pedestal configured to receive and secure a tabletop support on a top surface of the pedestal, and the tabletop support translates in at least one direction relative to the pedestal and the base; and a gantry ring having a bore and an image collection apparatus, the gantry ring coupled to the base and suspended above the top surface of the base, the gantry ring configured to translate along a length of the base between a first position adjacent to the pedestal to a second position adjacent to the second end of the base, the gantry ring further configured to rotate at least about 90 degrees with respect to an axis extending generally normal to the top surface of the base.

62. The medical imaging system of claim 61, wherein the base comprises a mobile base having one or more wheels attached to the base.

63. The medical imaging system of claim 61, further comprising:

a gimbal support connected to the base, the gantry ring being attached to the gimbal support and suspended above the top surface of the base.

64. The medical imaging system of claim 63, wherein the gantry ring translates and rotates by the translation and rotation of the gimbal support relative to the base.

65. The medical imaging system of claim 63, wherein the gimbal support comprises a generally U-shaped support having arms extending upwards from the base and connecting to opposite sides of the gantry ring, and the gantry ring is pivotable with respect to the gimbal support to tilt the gantry ring relative to the gimbal support and the base.

66. The medical imaging system of claim 61, wherein the image collection apparatus comprises an x-ray source and an x-ray detector array.

67. The medical imaging system of claim 61, further comprising a tabletop support mounted to and disposed above the pedestal, the tabletop support extending at least partially into the bore of the gantry ring, and wherein the tabletop support is detachable from the pedestal.

68. The medical imaging system of claim 67, wherein the tabletop support comprises a surgical or trauma table, or a chair for imaging a seated patient.

69. The medical imaging system of claim 67, wherein the tabletop support comprises a plurality of modular sections that can be added to and removed from the tabletop support to modify the configuration of the tabletop support.

70. The medical imaging system of claim 61, wherein the base has a length and a width, and the gantry translates over substantially the entire length of the base from the pedestal to the second end of the base, the gantry translating at least about one meter along the length of the base.

71. The medical imaging system of claim 61, wherein the gantry ring has an inner bore diameter that is greater than about 38 inches.

72. The medical imaging system of claim 71, wherein the bore diameter is between about 40 and 50 inches and the outer diameter of the gantry ring is less than about 70 inches.

73. The medical imaging system of claim 61, wherein the gantry ring has a width of about 17 inches or less.

74. The medical imaging system of claim 61, wherein the height of the pedestal above the top surface of the base is adjustable.

75. The medical imaging system of claim 61, further comprising a releasable locking mechanism for securing a tabletop support on a top surface of the pedestal.

76. The medical imaging system of claim 61, wherein the system comprises a mobile system and further comprises a drive mechanism for propelling the system.

77. The medical imaging system of claim 61, wherein the system comprises a computed tomography (CT) imaging system.

78. The medical imaging system of claim 61, wherein the system comprises a magnetic resonance imaging (MRI) system.

79. The medical imaging system of claim 61, wherein the gantry ring has an inner bore diameter that is greater than 38 inches, an outer diameter that is less than 70 inches, and a width of less than 17 inches.

80. The medical imaging system of claim 79, wherein the inner bore diameter is between about 40 and 50 inches, and the width of the gantry ring less than about 15 inches.

81. A medical imaging system, comprising:

a base having a top surface, a first end and a second end;

a pedestal connected to the base and positioned adjacent to the first end of the base, the pedestal extending in a vertical direction above the top surface of the base and configured to accept a plurality of interchangeable procedure-specific tabletop supports;

a gantry ring having a bore and an image collection apparatus, the gantry ring coupled to the base and suspended above the top surface of the base, the gantry ring configured to translate along a length of the base between a first position adjacent to the pedestal to a second position adjacent to the second end of the base, the gantry ring further configured to rotate at least about 90 degrees with respect to an axis extending generally normal to the top surface of the base; and a retractable support element that extends upwards from the base to support a cantilevered end of a tabletop support that is mounted to the pedestal.

82. The medical imaging system of claim 81, further comprising:

a gimbal support connected to the base, the gantry ring being attached to the gimbal support and suspended above the top surface of the base.

83. A medical imaging system, comprising:

a base having a top surface, a first end and a second end;

a pedestal connected to the base and positioned adjacent to the first end of the base, the pedestal extending in a vertical direction above the top surface of the base and configured to accept a plurality of interchangeable procedure-specific tabletop supports;

a tabletop support mounted to and disposed above the pedestal, the tabletop support extending at least partially into the bore of the gantry ring, the tabletop support comprising a plurality of modular sections that can be added to and removed from the tabletop support to modify the configuration of the tabletop support; and a gantry ring having a bore and an image collection apparatus, the gantry ring coupled to the base and positioned above the top surface of base, the gantry ring configured to translate along a length of the base between a first position adjacent to the pedestal to a second position adjacent to the second end of the base, the gantry ring further configured to rotate at least about 90 degrees with respect to an axis extending generally normal to the top surface of the base.

84. The medical imaging system of claim 83, further comprising:

a gimbal support connected to the base, the gantry ring being attached to the gimbal support and suspended above the top surface of the base.

85. A medical imaging system, comprising:
a base with a top surface, a first end and a second end;
a pedestal connected to the base and positioned adjacent to the first end of the base;
a gantry ring having a bore and an image collection apparatus, the gantry ring coupled to the base and positioned above the top surface of the base, the image collection apparatus operable to obtain image data of an object,
rotating means for rotating the gantry ring about an axis extending generally normal to the top surface of the base, the gantry ring rotating at least about 90 degrees from a transport position to an imaging position;
a tabletop support attachable to the pedestal, the tabletop support extending from the pedestal into an imaging area that is above the base and in the direction of the gantry ring, an object to be imaged being positionable on the tabletop support;
translating means for translating the gantry ring in a first direction relative to the base;
transporting means for transporting the tabletop support to the pedestal;
means for securing the tabletop support on the pedestal and for removing the tabletop support from the pedestal; and
means for adjusting the relative positions of the tabletop support and the gantry ring until a region of interest is located inside the bore of the gantry ring, the image collection apparatus obtaining image data of the region of interest.

86. The medical imaging system of claim 85, further comprising:
a gimbal support connected to the base, the gantry ring being attached to the gimbal support and suspended above the top surface of the base.

87. A method of imaging an object with a medical imaging system having a base with a top surface, a first end and a second end, a pedestal connected to the base and positioned adjacent to the first end of the base, and a gantry ring having a bore and an image collection apparatus, the gantry ring coupled to the base and positioned above the top surface of the base, the method comprising:
rotating the gantry ring about an axis extending generally normal to the top surface of the base, the gantry ring rotating at least about 90 degrees from a transport position to an imaging position;
attaching a tabletop support to the pedestal, the tabletop support extending from the pedestal into an imaging area that is above the base and in the direction of the gantry ring;
positioning an object to be imaged on the tabletop support;
translating the gantry ring in a first direction relative to the base;
obtaining image data of the object using the image collection apparatus on the gantry ring; and
rotating the pedestal and tabletop support relative to the base to bring the tabletop support into and out of the imaging area.

88. The method of claim 87, wherein the medical imaging system comprises a gimbal support connected to the base, and a the gantry ring is attached to the gimbal support and suspended above the top surface of the base.

89. The method of claim 88, wherein rotating the gantry ring comprises rotating the gimbal support with respect to the base, and translating the gantry ring comprises translating the gimbal support with respect to the base.

90. The method of claim 87, further comprising:
removing at least a portion of the tabletop support from the imaging area; and
rotating the gantry ring at least about 90 degrees from the imaging position to the transport position.

91. The method of claim 87, wherein the image collection apparatus comprises an x-ray source and x-ray detector array, and obtaining image data comprises rotating at least one of the x-ray source and the x-ray detector array around the interior of the gantry ring.

92. The method of claim 91, further comprising translating the gantry while at least one of the x-ray source and x-ray detector rotate in the gantry ring to perform a helical scan.

93. The method of claim 87, wherein the object being imaged comprises a human or animal patient.

94. The method of claim 93, further comprising performing a medical procedure on the patient while the patient is positioned on the tabletop support.

95. The method of claim 94, wherein the medical procedure comprises brachytherapy.

96. The method of claim 87, further comprising transporting the tabletop support to the pedestal using a mobile cart.

97. The method of claim 87, further comprising:
removing the tabletop support from the pedestal and providing a second tabletop support for a second imaging operation.

98. The method of claim 97, wherein at least one of the tabletop supports comprises a chair.

99. The method of claim 97, wherein at least one of the first and second tabletop supports comprises a procedure-specific tabletop support.

100. The method of claim 87, further comprising transporting the imaging system when the gantry ring is in the transport position.

101. The method of claim 100, wherein the imaging system is transported on wheels attached to the base.

102. The method of claim 87, further comprising:
positioning a patient on the tabletop support;
transporting the patient on the tabletop support to the imaging system; and
removing the patient and the tabletop support from the system after obtaining image data from the patient.

103. The method of claim 87, further comprising:
translating the gantry to at least one of a first position, proximate the pedestal, and a second position, proximate the second end of the base, when not obtaining images to provide access to the object being imaged.

104. The method of claim 87, wherein the gantry ring has an inner bore diameter that is greater than 38 inches, an outer diameter that is less than 70 inches, and a width of less than 17 inches.

105. The method of claim 104, wherein the inner bore diameter is between about 40 and 50 inches, and the width of the gantry ring less than about 15 inches.

* * * * *